(12) United States Patent
Tasci

(10) Patent No.: US 10,799,224 B2
(45) Date of Patent: Oct. 13, 2020

(54) DEVICE FOR LAPAROSCOPIC SURGERY

(71) Applicant: Ihsan Tasci, Fatih/Istanbul (TR)

(72) Inventor: Ihsan Tasci, Fatih/Istanbul (TR)

(73) Assignee: Ihsan TASCI, Istanbul (TR)

(*) Notice: Subject to any disclaimer, the term of this patent is extended or adjusted under 35 U.S.C. 154(b) by 94 days.

(21) Appl. No.: 16/090,517

(22) PCT Filed: Mar. 30, 2017

(86) PCT No.: PCT/TR2017/050129
§ 371 (c)(1),
(2) Date: Oct. 1, 2018

(87) PCT Pub. No.: WO2017/171686
PCT Pub. Date: Oct. 5, 2017

(65) Prior Publication Data
US 2019/0110782 A1    Apr. 18, 2019

(30) Foreign Application Priority Data
Mar. 30, 2016    (WO) .................. PCT/IB2016/051796

(51) Int. Cl.
*A61B 17/00*    (2006.01)
*A61B 17/29*    (2006.01)

(52) U.S. Cl.
CPC ........ *A61B 17/00234* (2013.01); *A61B 17/29* (2013.01); *A61B 2017/003* (2013.01); *A61B 2017/00309* (2013.01); *A61B 2017/00424* (2013.01); *A61B 2017/00738* (2013.01); *A61B 2017/291* (2013.01); *A61B 2017/2905* (2013.01)

(58) Field of Classification Search
CPC .............. A61B 17/00234; A61B 17/29; A61B 2017/00309; A61B 2017/00424; A61B 2017/00738; A61B 2017/2905; A61B 2017/291
See application file for complete search history.

(56) References Cited

U.S. PATENT DOCUMENTS

| | | |
|---|---|---|
| 2007/0021737 A1 | 1/2007 | Lee |
| 2010/0249497 A1 | 9/2010 | Peine et al. |
| 2012/0053415 A1 | 3/2012 | Bunch et al. |
| 2012/0253131 A1 | 10/2012 | Malkowski et al. |

*Primary Examiner* — Paula J Stice
(74) *Attorney, Agent, or Firm* — Maine Cernota & Rardin

(57) ABSTRACT

A surgical instrument having an elongated shaft that is at least partially bendable with a surgical tool coupled to a distal end of the elongated shaft and a handle coupled to a proximal end of the elongated shaft to manipulate the surgical tool and a bendable elongated guide coupled to the handle to support the surgical instrument.

13 Claims, 4 Drawing Sheets

DEVICE FOR LAPAROSCOPIC SURGERY

TECHNICAL FIELD OF THE INVENTION

The present invention relates to a device for surgery, and more particularly to a manually operated device for laparoscopic surgery.

BACKGROUND OF THE INVENTION

Manually operated laparoscopic instruments having articulated bodies are known to control the orientation of the instrument during the surgery. However, the laparoscopic instruments comprising such articulation features do not have enough stability. Therefore, a surgery tool attached to such a laparoscopic instrument cannot be controlled precisely to perform a laparoscopic surgery. Further, when a plurality of the laparoscopic instruments comprising such articulation features is used during a laparoscopic surgery, they obstruct each other when placed through the same incision.

Accordingly, an object of the present invention is to provide a laparoscopic surgery instrument having a stable structure, which is bendable and which provides more freedom at an operation site.

SUMMARY OF THE INVENTION

Current invention is defined by the appended claims, the content of which is included here by reference.

The present invention provides a device for laparoscopic surgery comprising:
- an elongated shaft that is at least partially bendable;
- a distal tool coupled to a distal end of the elongated shaft;
- a handle coupled to a proximal end of the elongated shaft to manipulate the distal tool;
- an elongated guide supporting the elongated shaft and coupled at a proximal end thereof to the handle, wherein the elongated guide is at least partially bendable; and
- a first control unit arranged between the handle and the elongated guide to control bending of the elongated guide and a second control unit arranged between the handle and the elongated shaft to control bending of the elongated shaft.

According to the invention, bending of the elongated guide and at least partially the bending of the elongated shaft may be controlled by the handle independently and/or in different directions via the first control unit and the second control unit.

According to the present invention, the elongated guide and the elongated shaft may comprise respective bendable portions and may be bent together. Accordingly, a bending motion of the elongated guide may bend the elongated shaft correspondingly.

According to the present invention, the elongated guide may support the elongated shaft at least at a distal end of the elongated guide. The elongated guide may comprise a body extending longitudinally between the proximal end and the distal end thereof in form of a sleeve accommodating the elongated shaft at least partially.

According to the present invention, the elongated guide and the elongated shaft may extend longitudinally substantially parallel to each other.

According to the present invention, the elongated guide may be pivotally coupled to the handle, preferably such that a pivoting motion of the handle with respect to the elongated guide bends the elongated guide. The handle and the elongated guide may be coupled to each other via a first joint, which may be a ball joint or a hinge. The handle may be arranged in a pivotable, rotatable or tiltable manner with respect to the elongated guide via the first joint, preferably in two opposite directions such that the elongated guide can be bent on a plane comprising the two directions in response to the motion of the handle about the first joint. According to the present invention, the elongated guide may substantially replicate the motion of the handle about the first joint.

According to the present invention, the handle may be pivotally coupled to the elongated shaft, preferably such that a pivoting motion of the handle with respect to the elongated shaft bends the elongated shaft, preferably at a bendable part extending from the distal end of the elongated guide. The handle and the elongated shaft may be coupled to each other via a second joint, which may be a ball joint or a hinge. The handle may be arranged in a pivotable, rotatable or tiltable manner with respect to the elongated shaft via the second joint, preferably in four orthogonal directions such that the elongated guide can be bent on orthogonal planes each comprising one of the four orthogonal directions in response to the motion of the handle about the second joint. According to the present invention, the elongated shaft may substantially replicate the motion of the handle about the second joint.

The first control unit may comprise a first line coupled to the elongated guide at a first side of the elongated guide preferably near the distal end and to the handle and arranged to extend along the elongated guide and the first joint and a second line coupled to the elongated guide at a second side of the elongated guide preferably near the distal end and to the handle and arranged to extend along the elongated guide and the first joint such that when the handle is rotated about the first joint, one of the first line and the second line is pulled by the handle such that the elongated guide bends at one of the first side and the second side. The first side is preferably substantially opposite to the second side to provide counter control of bending. The first line and the second line may each comprise a respective cable.

The second control unit may comprise a first line coupled to the elongated shaft at a first side of the elongated shaft preferably near the distal end and to the handle and arranged to extend along the elongated shaft and the second joint; and a second line coupled to the elongated shaft at a second side of the elongated shaft preferably near the distal end and to the handle and arranged to extend along the elongated shaft and the second joint; and a third line coupled to the elongated shaft at a third side of the elongated shaft preferably near the distal end and to the handle and arranged to extend along the elongated shaft and the second joint; and a fourth line coupled to the elongated shaft at a fourth side of the elongated shaft preferably near the distal end and to the handle and arranged to extend along the elongated shaft and the second joint such that when the handle is rotated about the second joint, one or more of the first line, the second line, the third line and the fourth line is pulled by the handle such that the elongated guide bends at one or more of the first side, the second side, the third side and the fourth side that are preferably substantially orthogonal to each other to provide counter control of bending. The first line, the second line, the third line and the fourth line may each comprise a respective cable.

According to the present invention, the elongated guide and/or the elongated shaft may comprise lateral slits thereon to enable bending.

According to the present invention, the elongated shaft may be more elastic than the elongated guide. Preferably, the elongated guide may be made from a metallic material and/or the elongated shaft may be made from a plastics material. Alternatively or in addition, the lateral slits of the elongated guide may extend substantially on the first side and on the second side thereof, preferably sequentially in lateral direction; and/or the at least some of the lateral slits of the elongated shaft may extend substantially on the first side, the second side, the third side and the fourth side thereof, preferably sequentially in lateral direction. Preferably the lateral slits of the elongated shaft near the proximal end thereof may extend substantially on the first side and on the third side opposite to the first side, preferably sequentially in lateral direction.

According to the present invention, the elongated shaft may comprise a manipulation line between the distal tool and the handle to manipulate the distal tool, preferably comprising a cable, that may be arranged preferably to extend along and/or through the elongated shaft, wherein the handle can pull the manipulation line preferably via a trigger arranged thereon to manipulate the distal tool.

According to the present invention, the elongated guide may comprise a curvature or a curved portion near the proximal end.

According to the present invention, the first control unit and/or the second control unit are covered and/or shielded by respective sleeves. The manipulation line is arranged to extend through the second control unit and the second control unit is arranged to extend through the first control unit.

The first joint and/or the second joint may comprise locking elements to fix their orientation during surgery.

According to the present invention, the handle may comprise a first body part coupled to the first control unit and a second body part coupled to the second control unit, wherein the first body part and the second body part are pivotally coupled. The first joint is arranged between the first body part and the elongated guide. The second joint is arranged between the elongated shaft and the second body part. When the first body part rotates with respect to the second body part, the second joint rotates accordingly.

According to the present invention, the handle is coupled to the elongated shaft, the elongated guide and the surgical tool, wherein the handle is able to manipulate the surgical tool and to bend the elongated guide and the elongated shaft to different directions and/or independently.

These and further advantages of the current invention are disclosed in the appended claims.

DESCRIPTION OF THE DRAWINGS

The above disclosed and further features of the current invention will be better understood with the following detailed description and drawings of the preferred embodiments of the invention.

DESCRIPTION OF PREFERRED EMBODIMENT

A preferred embodiment of the current invention will be described with references to the appended drawings.

Figure 1:
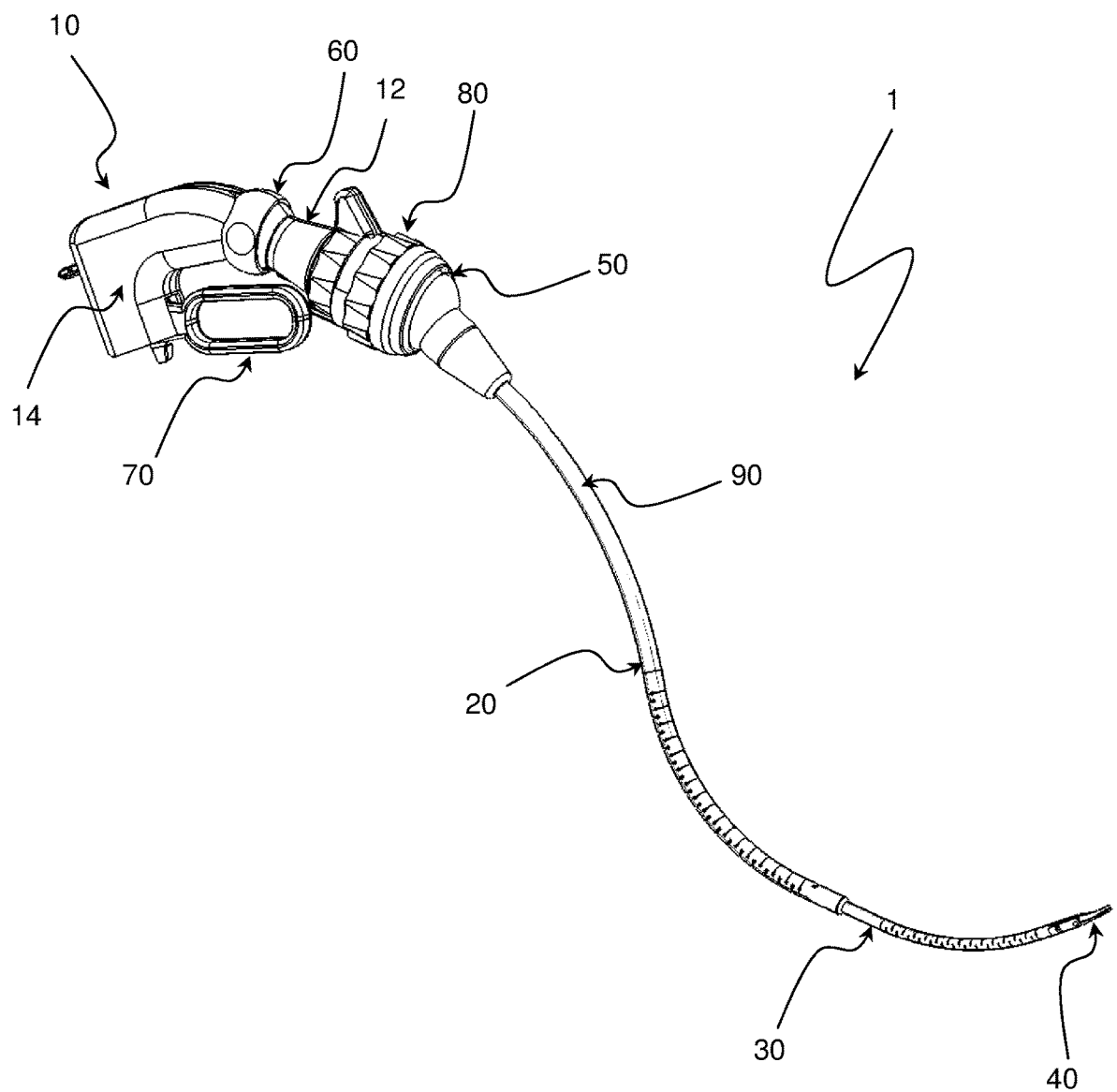
FIG. 1 shows a preferred embodiment of the present invention.

FIG. 1 shows a device 1 for laparoscopic surgery. The device 1 for laparoscopic surgery comprises a bendable elongated shaft 30 having a distal tool 40 at a distal end thereof. A handle 10 is coupled to the elongated shaft 30 at a proximal end thereof to manipulate the distal tool 40 during a surgery. The elongated shaft 30 extends through a bendable elongated guide 20 that is also coupled to the handle 10. The elongated shaft 30 and the elongated guide 20 comprise bendable portions near to their distal ends. The elongated guide 20 comprises a longitudinal body having a curvature form 90 at a region next the proximal end of the elongated guide 20. In order to support the elongated shaft 30, the elongated guide 20 is made more rigid than the elongated shaft 30. The elongated guide 20 comprises a body extending longitudinally between a proximal end and the distal end thereof in form of a sleeve accommodating the elongated shaft 30 at least partially.

Figure 2:
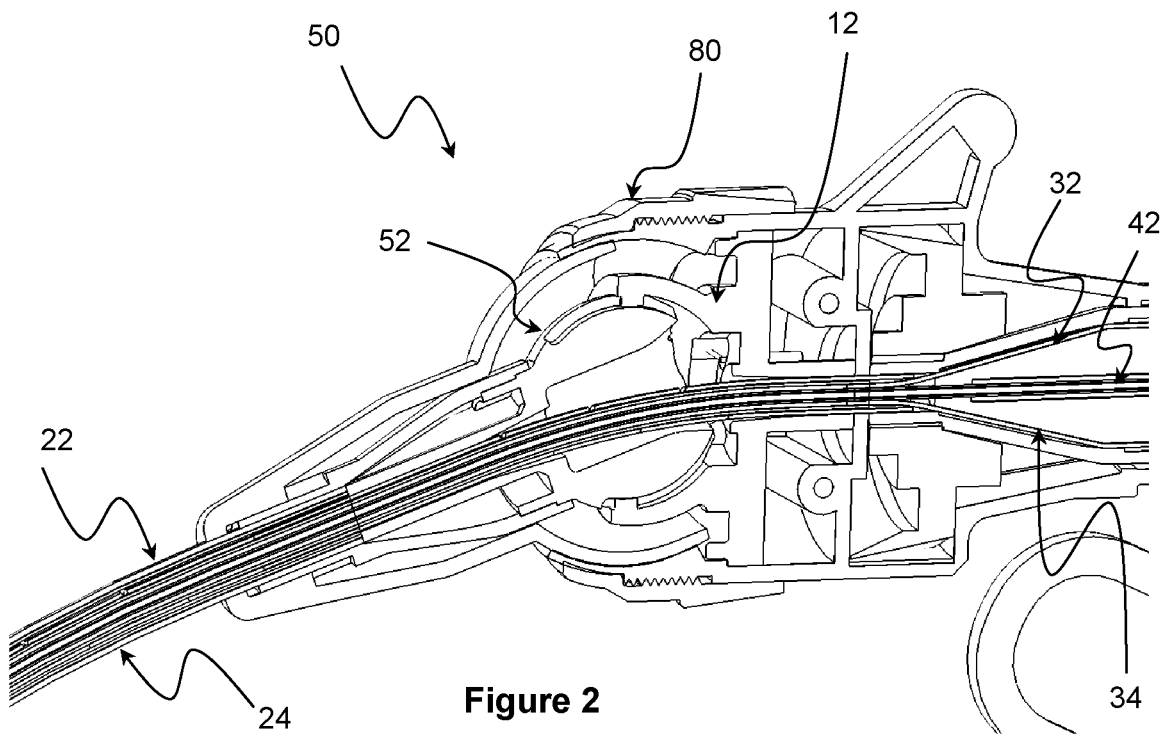
FIG. 2 shows a partial cross sectional view of a handle of the preferred embodiment of the present invention.

FIG. 2 shows a detailed cross sectional view of a first joint 50 arranged between the elongated guide 20 and the handle 10. The elongated guide 20 is coupled to a first body part 12 of the handle 10 via the first joint 50 comprising a ball joint 52.

Figure 7:
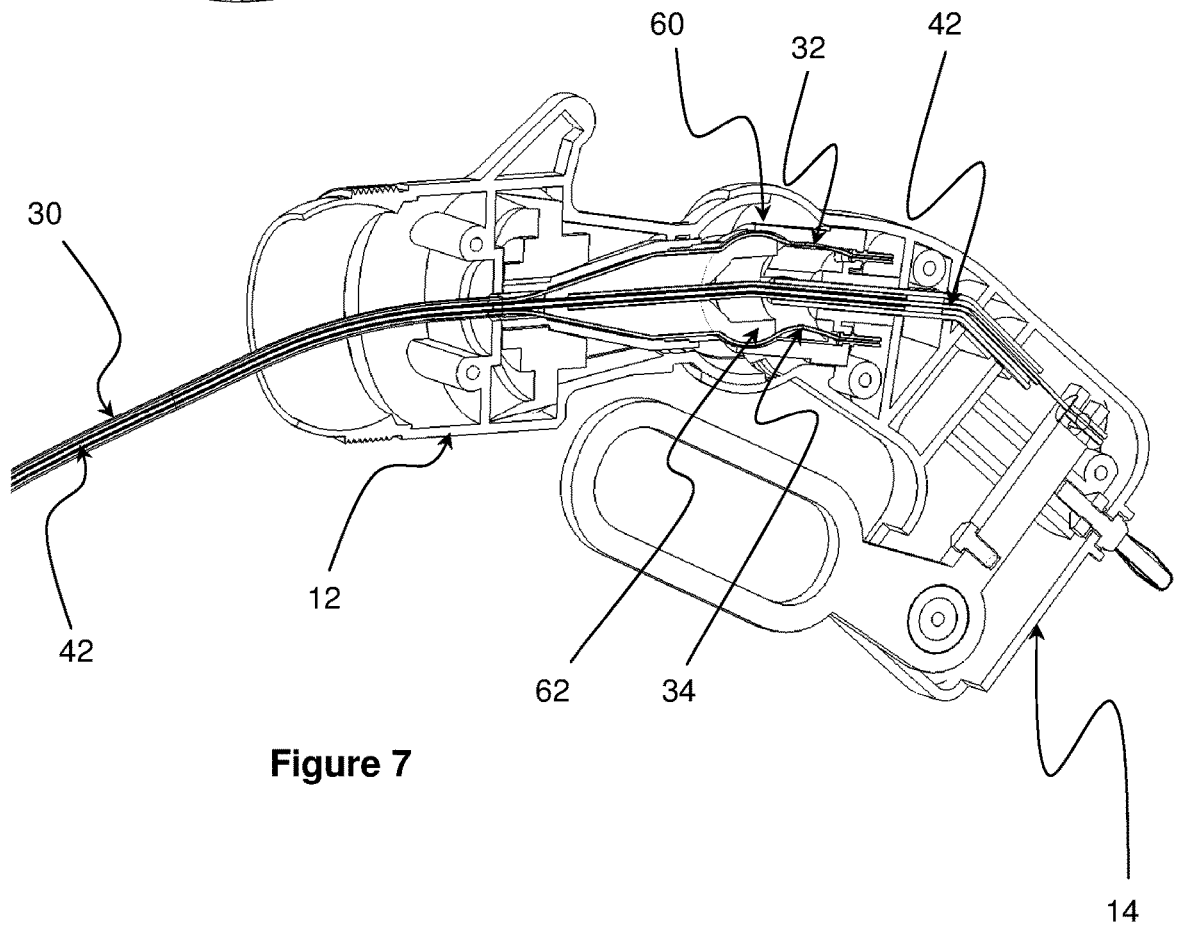
FIG. 7 shows a cross sectional view of a handle of the preferred embodiment of the present invention.

FIG. 7 shows a detailed cross sectional view of a second joint 60. The elongated shaft 30 is coupled to a second body part 14 of the handle 10 via the second joint 60 comprising a ball joint 62. The first body part 12 and the second body part 14 of the handle 10 are pivotally connected to each other via the second joint, since the second joint is supported by the first body part 12 and the second body part 14. A manipulation line 42 extends through the elongated shaft 30 that is coupled to the first body part 12. The manipulation line 42 extends from the distal tool 40 through the second joint 60 and couples to a trigger 70 arranged at the second body part 14. The trigger 70 manipulates the distal tool 40 by pulling and pushing the manipulation line 42.

Figure 3:
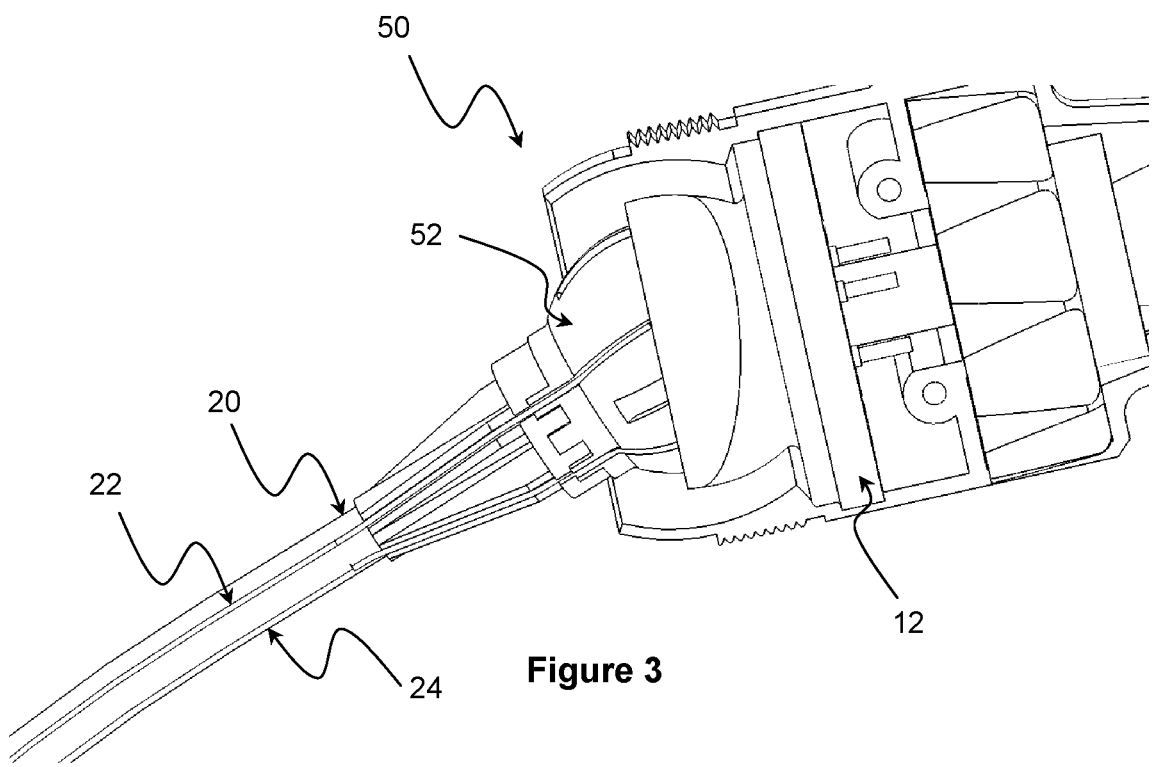
FIG. 3 shows another view of a part of the preferred embodiment of the present invention.

FIG. 3 shows a side view of the first joint 50 provided at the proximal end of the elongated guide 20. A first control unit 22, 24 is arranged between the handle and the elongated guide to control bending of the elongated guide by the handle.

Figure 5:
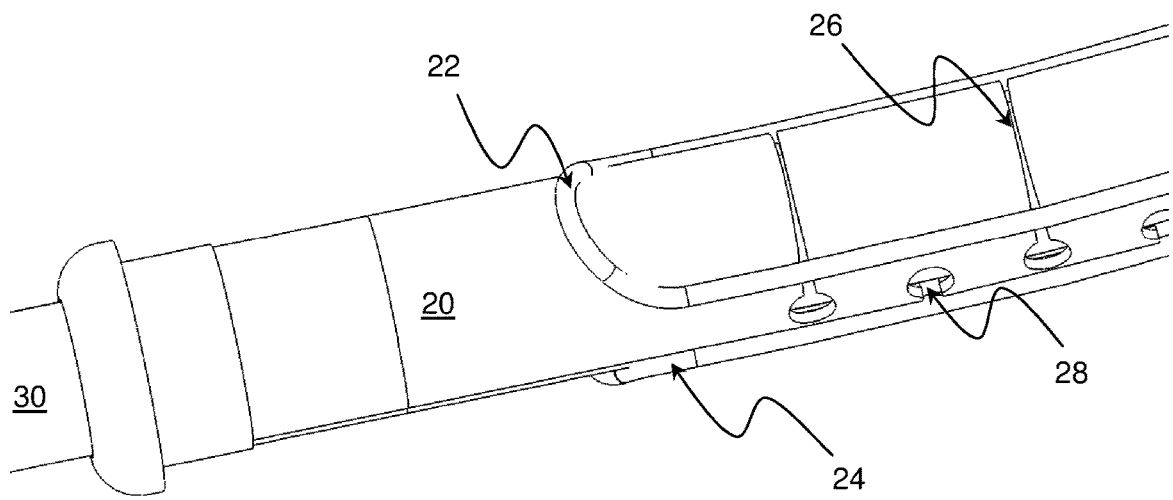
FIG. 5 shows a detailed view of an elongated guide of the preferred embodiment of the present invention.

The first control unit 22, 24 comprises a first line 22 coupled to the elongated guide at a first side of the elongated guide near its distal end and to the first body part 12 of the handle 10 and arranged to extend along the elongated guide 20 and the ball joint 52 and a second line 24 coupled to the elongated guide 20 at an opposing second side of the elongated guide 20 near its distal end and to the first body part 12 of the handle 10 and arranged to extend along the elongated guide 20 and the ball joint 52. Accordingly, the elongated guide 20 and the ball joint 52 comprise longitudinal grooves to support the first line 22 and the second line 24 along their surfaces. When the handle 10, specifically the first body part 12 is rotated about the ball joint 52, one of the first line 22 and the second line 24 is pulled by the handle 10 such that the elongated guide 20 bends to the side of the pulled line. The first line 22 and the second line 24 are made of cable or wire. In the preferred embodiment, the first line 22 and the second line 24 comprise each two parallel cables as shown in FIG. 5.

Figure 4:
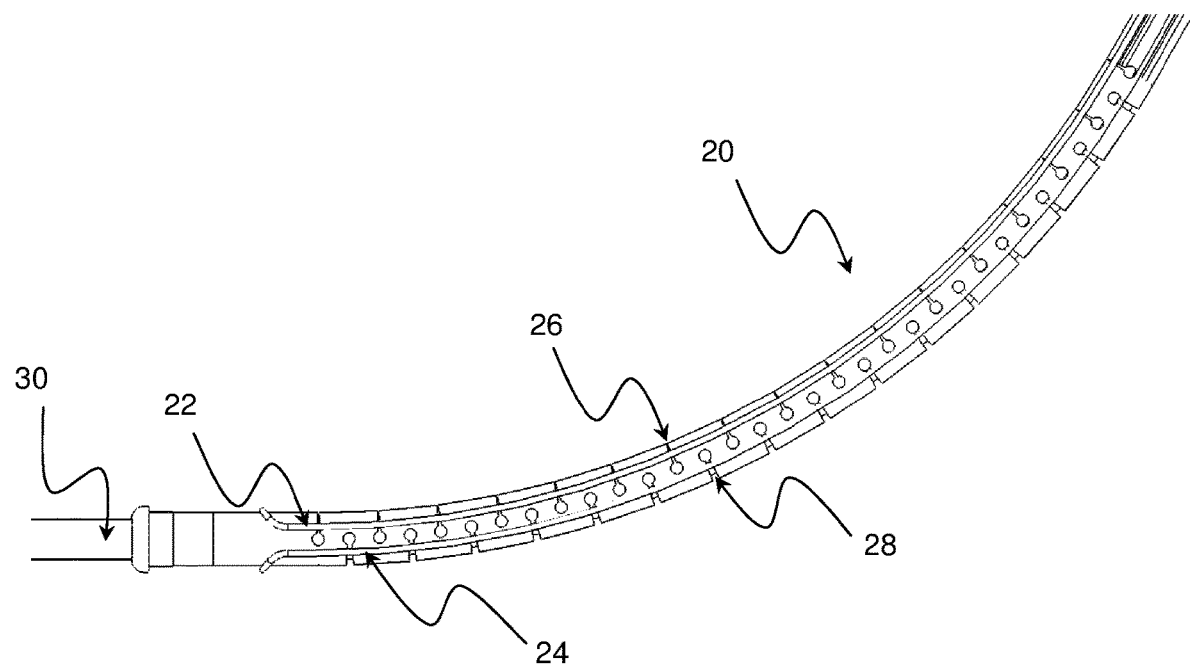
FIG. 4 shows a view of an elongated guide of the preferred embodiment of the present invention.

FIG. 4 shows the elongated guide 20 in a bended state to the side of the first line 22. The elongated guide 20 comprises a plurality of lateral slits 26 on the side of the first line 22 and a plurality of sequentially arranged opposing slits 28 on the side of the second line 24. Here, the first body part 12 of handle 10 has been tilted or rotated towards the side of the second line 24. Because of the tilting motion towards the side of the second line 24, the first body part 12 has pulled the first line 22 along the elongated guide 20 and the slits 26 on the side of the first line 22 have been squeezed.

Figure 6:
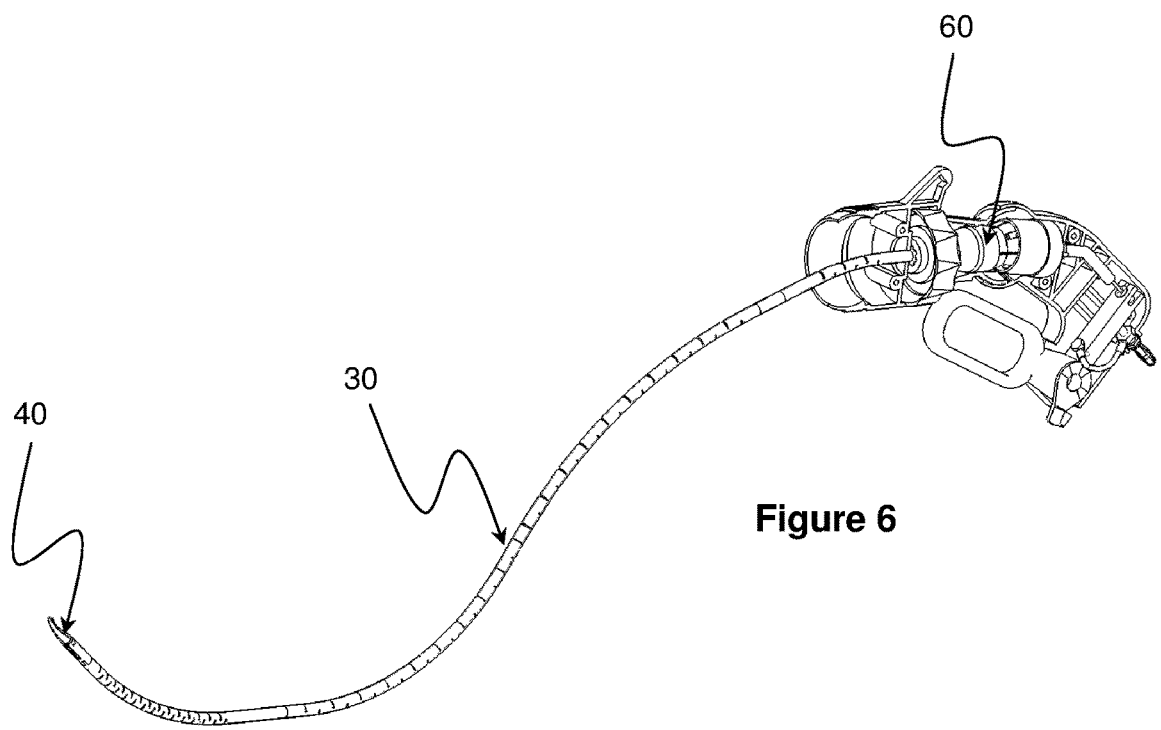
FIG. 6 shows a view of an elongated shaft and a handle of the preferred embodiment of the present invention.

FIG. 6 shows the elongated shaft 30 extending through the first body part 12 of the handle 10 hence also through the first joint 50 to the second joint 60. The elongated shaft 30 comprises a bendable part near its distal end next to the distal tool 40 that is controlled by the handle 10. The other part of the elongated shaft 30 that extends through the elongated guide 20 is also bendable according to the bending of the elongated guide 20. Therefore, the elongated shaft 30 comprises lateral slits thereon distributed circumferentially to enable bending in all directions.

In the preferred embodiment, the elongated guide is made of a metallic material and the elongated shaft is made of a plastics material.

FIG. 7 shows a second control unit 32, 34 arranged between the second body part 14 of the handle 10 and the elongated shaft 30 to control bending of the elongated shaft 30 by the handle. The second control unit 32, 34 comprises a first line 32, a second line (not shown), a third line 34 and a fourth line (not shown) each coupled to the distal end of the elongated shaft circumferentially orthogonally and all extending orthogonally along the elongated shaft and the second joint between the distal end of the elongated shaft 30 and the handle 10 such that when the second body part 14 of the handle 10 is rotated about the ball joint 62 of the second joint 60, one or more of the first line 32, the second line, the third line 34 and the fourth line is pulled by the second body part 14 of the handle 10 to bend the elongated shaft 30 towards the side of the pulling line. As shown FIG. 7, when the second body part 14 of the handle 10 is rotated about the second joint 60 towards the trigger 70, the third line 34 has become loose and the first line 32 on the opposite side has been pulled by the second body part 14.

The first joint 50 and the second joint 60 comprise locking elements 80 to fix their orientation during surgery.

The device 1 provides a support to the elongated shaft 30 and the distal tool 40 by the elongated guide 20 during the surgery, while the elongated guide 20, the elongated shaft 30, and the distal tool 40 can be oriented or manipulated by the first body part 12 and the second body part 14 of the handle 10 and the trigger 70 respectively independent from each other enabling more operation freedom to a surgeon.

The design features of the device, such as the number and the location of the lines and cables, size and orientation of the bending parts and joint types and materials, may all be adapted according to different cases appropriately.

The preferred embodiment of the invention is described above in the Drawings and Description of Preferred Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

The invention claimed is:

1. A device for laparoscopic surgery comprising:
an elongated shaft that is at least partially bendable;
a distal tool coupled to a distal end of the elongated shaft;
a handle coupled to a proximal end of the elongated shaft to manipulate the distal tool;
an elongated guide supporting the elongated shaft and coupled at a proximal end thereof to the handle, wherein the elongated guide is at least partially bendable; and
a first control unit arranged between the handle and the elongated guide to control bending of the elongated guide by the handle and a second control unit arranged between the handle and the elongated shaft to control bending of the elongated shaft by the handle;
wherein the elongated guide is pivotally coupled to the handle via a first joint comprising a ball joint, the first control unit comprises a first line extending along the elongated guide and the first joint and a second line extending opposite to the first line along the elongated guide and the first joint between the distal end of the elongated guide and the handle, and the elongated guide and the ball joint comprise longitudinal grooves to support the first line and the second line along their surfaces.

2. The device according to claim 1, wherein the elongated guide is arranged to support the elongated shaft at least at a distal end of the elongated guide.

3. The device according to claim 1, wherein the elongated guide comprises a body extending longitudinally between a proximal end and the distal end thereof in form of a sleeve accommodating the elongated shaft at least partially.

4. The device according to claim 1, wherein the elongated guide is pivotally coupled to the handle such that a pivoting motion of the handle about the first joint bends the elongated guide.

5. The device according to claim 1, wherein the handle is pivotally coupled to the elongated shaft via a second joint such that a pivoting motion of the handle about the second joint bends the elongated shaft, wherein the second joint preferably comprises a ball joint.

6. The device according to claim 1, wherein when the handle is rotated about the first joint, one of the first line and the second line is pulled by the handle to bend the elongated guide towards the pulling line.

7. The device according to claim 1, wherein the second control unit comprises a first line, a second line, a third line and a fourth line extending orthogonally along the distal end of the elongated shaft end the handle such that when the handle is rotated about the second joint, one or more of the first line, the second line, the third line and the fourth line is pulled by the handle to bend the elongated shaft towards the pulling line.

8. The device according to claim 1, wherein the elongated guide and/or the elongated shaft comprise lateral slits thereon to enable bending.

9. The device according to claim 1, wherein the elongated shaft is more elastic than the elongated guide, preferably the elongated guide is made of a metallic material and/or the elongated shaft is made of a plastics material.

10. The device according to claim 9, wherein the lateral slits of the elongated guide extend on opposite sides thereof, preferably sequentially in lateral direction; and/or at least part of the lateral slits of the elongated shaft extend circumferentially, preferably sequentially in lateral direction.

11. The device according to claim 1, wherein the elongated shaft comprises a manipulation line between the distal tool and the handle to manipulate the distal tool, preferably extending along and/or through the elongated shaft, wherein the handle can pull the manipulation line preferably via a trigger arranged thereon to manipulate the distal tool.

12. The device according to claim 1, wherein the elongated guide comprises a curvature or a curved portion near its proximal end.

13. The device according to claim 1, wherein the handle comprises a first body part coupled to the first control unit and a second body part coupled to the second control unit, wherein the first body part and the second body part are pivotally coupled to each other preferably such that when the first body part rotates with respect to the second body part, the second joint rotates accordingly.

\* \* \* \* \*